(12) United States Patent
Sebban et al.

(10) Patent No.: US 11,103,653 B2
(45) Date of Patent: Aug. 31, 2021

(54) DEVICE FOR INSERTING A BLUNT-TIP CANNULA UNDER THE SKIN OF A PATIENT

(71) Applicant: SOFT MEDICAL AESTHETICS, Paris (FR)

(72) Inventors: Sandrine Sebban, Levallois Perret (FR); Jean Yves Corbin, Le Fresne Camilly (FR); Maxime Vaupres, Grentheville (FR); Mathias D'Estais, Caen (FR); Isabelle Jeanson, Paris (FR)

(73) Assignee: SOFT MEDICAL AESTHETICS, Paris (FR)

(*) Notice: Subject to any disclaimer, the term of this patent is extended or adjusted under 35 U.S.C. 154(b) by 71 days.

(21) Appl. No.: 15/329,427

(22) PCT Filed: Aug. 4, 2015

(86) PCT No.: PCT/FR2015/052150
§ 371 (c)(1),
(2) Date: Jan. 26, 2017

(87) PCT Pub. No.: WO2016/020617
PCT Pub. Date: Feb. 11, 2016

(65) Prior Publication Data
US 2017/0209654 A1    Jul. 27, 2017

(30) Foreign Application Priority Data

Aug. 4, 2014  (FR) ........................................ 1457592

(51) Int. Cl.
*A61M 5/32*    (2006.01)
*A61M 25/06*   (2006.01)
*A61M 5/31*    (2006.01)

(52) U.S. Cl.
CPC ........ *A61M 5/3287* (2013.01); *A61M 5/3137* (2013.01); *A61M 25/065* (2013.01); *A61M 25/0637* (2013.01); *A61M 25/0643* (2013.01)

(58) Field of Classification Search
CPC .............. A61M 25/065; A61M 5/3287; A61M 25/0637; A61M 25/0643; A61M 25/0668;
(Continued)

(56) References Cited

U.S. PATENT DOCUMENTS 3,537,451 A * 11/1970 Beck ..................... A61M 25/06
604/165.03
3,611,965 A    10/1971 Lange
(Continued)

OTHER PUBLICATIONS

International Search Report for International Application No. PCT/FR2015/052150, dated Nov. 2, 2015.

*Primary Examiner* — Brandy S Lee
*Assistant Examiner* — Hong-Van N Trinh
(74) *Attorney, Agent, or Firm* — Marshall, Gerstein & Borun LLP (57) ABSTRACT

A device for inserting a blunt-tip cannula under the skin of a patient with a view to injecting a biocompatible product, including a central body equipped with a groove that extends along a sagittal plane while having a sharp distal tip projecting from a distal end of the body in order to pierce the skin, the groove being arranged to allow the cannula to slide along same beyond the distal tip towards at least one area to be treated located under the skin, the central body being provided with two lateral gripping arms that extend symmetrically on either side of the sagittal plane in a transverse direction that forms, with the sagittal plane, an angle (α) of between 30° and 85°, each gripping arm further having a finger grip surface that has a front central portion located at a distance between 8 mm and 30 mm from the distal end of the central body.

13 Claims, 6 Drawing Sheets

(58) Field of Classification Search
CPC .............. A61M 25/06; A61M 25/0662; A61M 25/0612; A61M 25/0606; A61M 25/0618; A61M 25/0625; A61M 25/0631; A61M 2025/0656; A61M 25/0097; A61B 17/3415

See application file for complete search history.

(56) References Cited

U.S. PATENT DOCUMENTS

| | | | | |
|---|---|---|---|---|
| 3,630,198 | A * | 12/1971 | Henkin | A61M 25/065 604/170.01 |
| 3,827,434 | A * | 8/1974 | Thompson | A61M 25/065 604/160 |
| 4,354,491 | A * | 10/1982 | Marbry | A61M 25/065 604/160 |
| 4,449,973 | A | 5/1984 | Luther | |
| 5,741,284 | A | 4/1998 | Karlsson | |
| 5,853,391 | A * | 12/1998 | Bell | A61B 17/3401 604/160 |
| 6,027,480 | A * | 2/2000 | Davis | A61M 25/0606 604/164.05 |
| 2004/0098020 | A1* | 5/2004 | Nardeo | A61M 25/0668 606/194 |

* cited by examiner

DEVICE FOR INSERTING A BLUNT-TIP CANNULA UNDER THE SKIN OF A PATIENT

CROSS-REFERENCE TO RELATED APPLICATION

The present application is the US national phase of International Application No. PCT/FR2015/052150, filed Aug. 4, 2015, which application claims priority to French Application No. FR 1457592, filed Aug. 4, 2014. The priority application, FR 1457592, is hereby incorporated by reference.

FIELD OF THE DISCLOSURE

The invention relates to a device for inserting a blunt-tip cannula under the skin of a patient with a view to injecting a biocompatible product, a kit for injecting comprising such a device and at least one blunt-tip injection cannula, as well as a method for injecting within the framework of an aesthetic intervention a biocompatible product using such a kit.

BACKGROUND

It applies in particular to injections of a filler product, in particular with a hyaluronic acid base, under the skin of at least one portion of the body of a patient, for example of the face and/or of the neck of the patient, in order to temporarily make the effects deemed as unsightly of the ageing of the skin disappear, such as example wrinkles and slackening of the skin, and/or to revitalize the skin by hydrating the layers of the epidermis.

It can also apply to autograft injections of autologous organic products sampled beforehand on the patient, such as platelet-rich plasma (PRP), for example for a fibroblastic and collagen stimulation of the skin with a view to correcting the unsightly effects due to the ageing thereof, or of fat, for example to correct the losses of volume of the skin due to trauma such as an accident or surgery.

In order to practice such an intervention, the practitioner generally uses an injection cannula that has a blunt tip and at least one lateral injection orifice arranged in the vicinity of the blunt tip. Indeed, this type of cannula is particularly suited for filler products, which are generally rather thick, and makes it possible to minimise trauma to the tissue and vessels of the deep layers of the skin, such as hematomas, bruises or oedemas, as well as nerve injury.

During the intervention, the practitioner begins by piercing, with a needle that has a sharp distal tip, a zone of the skin located not far from an area to be treated, so as to arrange access to the area to be treated.

In particular, the practitioner uses a standard injection needle provided with a base made of plastic normally arranged to allow for the mounting of the needle on the tip of a syringe, and carries out the piercing of the skin by grasping the base with two fingers, which constitutes misuse of the needle.

Then, the practitioner removes the piercing needle and inserts via the hole arranged as such an injection cannula such as described hereinabove, then slides the cannula under the skin until the injection orifice reaches the area to be treated. The practitioner then injects the product into the area to be treated by the intermediary of the cannula, with the product being contained for example in a syringe or in another type of container on which the cannula is mounted.

However, this type of technique does not provide entire satisfaction, in that it requires usage in two separate steps, insofar as the practitioner must first completely remove the needle from the skin before being able to insert the injection cannula. In particular, the successive entering and exiting of the needle then of the cannula cause trauma to the skin tissues.

Furthermore, the hole formed by the piercing needle is sometimes difficult to locate, in particular because the practitioner has to remove the needle and place it on a sterile surface before grasping the injection cannula, and therefore momentarily looks away from the pierced zone. As such, the practitioner can waste time trying to locate the hole.

In particular, to locate the hole, the practitioner may be forced to pinch the skin, sometimes several times, so as to cause bleeding through the hole, which may be painful for the patient and generate hematomas, and even a swelling of the pinched zone for the purpose of bleeding. Therefore, recovery of the patient is extended, and the presence of unsightly traces can constitute a prejudice for the patient, then forced to temporary social eviction during the recovery.

In addition, even if the practitioner locates the hole, he must also memorise the angle of incidence of the needle. Indeed, if he does not respect the same angle, the cannula can forge another path in the epidermis and as such increase the lesion.

Moreover, such a technique requires many manipulations of the piercing needle, in particular for inserting it and for removing it from the skin of the patient, which increases the risk of accidental pricks for the practitioner as well as the risk of loss of sterility of the needle, with the risks of accidental pricks being all the more so increased in that the handling of the needle lacks in ergonomy, insofar as the needle is not especially suited for such a use.

The invention aims to improve prior art by proposing in particular a device that allows the practitioner to more easily and more quickly carry out the insertion under the skin of an injection cannula, and therefore the injection of a product, and this while still substantially decreasing the risk of trauma for the patient.

To this effect, according to a first aspect, the invention proposes a device for inserting a blunt-tip cannula under the skin of a patient with a view to injecting a biocompatible product, the device comprising a central body equipped with a groove that extends along a sagittal plane while having a sharp distal tip projecting from a distal end of the body in order to pierce the skin, the groove being arranged to allow the cannula to slide along same beyond the distal tip towards at least one area to be treated located under the skin, the central body being provided with two lateral gripping arms that extend symmetrically on either side of the sagittal plane in a transverse direction that forms, with the sagittal plane, an angle between 30° and 85°, each gripping arm further having a finger grip surface that has a front central portion located at a distance between 8 mm and 30 mm from the distal end of the central body.

According to a second aspect, the invention proposes a kit for injecting a biocompatible product, the kit comprising such a device for inserting as well as at least one blunt-tip injection cannula, the groove being arranged to allow for the sliding on same of the at least one cannula beyond its distal tip towards at least one area to be treated located under the skin of a patient.

According to a third aspect, the invention proposes a method for injecting within the framework of an aesthetic intervention a biocompatible product by means of such a kit, the method providing the following successive steps of:

grasping the device by the intermediary of the finger grip surface of at least one of the grasping arms;

piercing a zone of the skin of a patient by means of the sharp distal tip;

arranging an injection cannula on the groove;

sliding the injection cannula beyond the sharp distal tip, so as to insert the blunt tip under the skin;

removing the device so as to extract the sharp tip from the skin by leaving the cannula inserted under the skin.

BRIEF DESCRIPTION OF THE SEVERAL VIEWS OF THE DRAWINGS

Other particularities and advantages of the invention shall appear in the following description, given in reference to the annexed figures, wherein.

DETAILED DESCRIPTION OF THE PREFERRED EMBODIMENTS

In relation with these figures, a device is described hereinbelow for inserting a blunt-tip cannula under the skin of a patient with a view to injecting a biocompatible product, a kit for injecting comprising such a device and at least one blunt-tip injection cannula, as well as a method for injecting within the framework of an aesthetic intervention of a biocompatible product using such a kit.

The kit for injecting can also be used for the injecting of a biocompatible product within the framework of a medical or veterinary intervention, the product containing for example mainly an anaesthetic. In particular, the kit for injecting can be a single-use medical device intended to be used by qualified personnel, in particular by medical or paramedical personnel.

Within the framework of an aesthetic intervention, the product to be injected can be a filler product, for example with a hyaluronic acid base, in order to temporarily correct the unsightly effects of the ageing of the skin. In particular, a product with a fluid hyaluronic acid base can be used to smooth the skin in order to attenuate wrinkles. Likewise, a product with a cross-linked hyaluronic acid base, therefore thicker, can be used to give volume back to the skin and/or to stretch the skin, in order to counterbalance a slackening due to a loss of elasticity of the skin and/or to correct an asymmetry, in the case where a zone of the skin has a slackening and/or a loss of volume more substantial than its symmetrical zone.

The product to be injected can also comprise an additive that has anaesthetic properties, for example with a lidocaine base, in order to reduce the pain that the patient may feel during the injection, with this pain being all the more so substantial that the product is thick. The product to be injected can also comprise an additive that has antioxidant properties, for example with a mannitol base, as well as vitamins to revitalize the layers of the skin in the area to be treated.

The product to be injected can also be an autologous organic product sampled beforehand on the patient, such as for example fat or platelet-rich plasma (PRP), for purely aesthetical purposes and/or so as to allow for autograft injections, in particular to correct the unsightly effects due to trauma such as an accident or surgery.

The area to be treated can be located on the face or the neck of the patient, in particular on the portions of the face or of the neck that are the most subject to unsightly effects of ageing of the skin, such as wrinkles or slackening.

For example, the area to be treated can be located at a corner of the lips (subject to "bitterness folds"), at an external corner of an eye (subject to "crow's foot" wrinkles), on a temple, on the forehead, and in particular on the glabella (subject to "lion wrinkles"), on an orbital zone (where circles and/or pockets can appear), of the tear trough (located under an eye) of a cheekbone or of a cheek (where a slackening and/or a loss of volume of the skin can be observed).

The area to be treated can also be located on other portions of the body in particular subject to such effects of ageing, such as the hands, but also the arms, the thighs, the chest for women, in particular on the neckline, the scalp, the belly, or the feet.

According to the product to be injected and the desired aesthetic effect, the area to be treated can be located at various depths of the skin of the patient. For example, in order to correct wrinkles, the area to be treated is generally located in a surface layer of the skin, in particular the epidermis or the dermis. On the contrary, for correcting a slackening of the skin, a lack of volume, and any resulting asymmetry, the area to be treated is rather located in a deep layer of the skin, in particular of the hypodermis.

In particular, the area to be treated can be located in the stratum granulosum, i.e. the last layer of nucleated cells of the epidermis. The area to be treated can also be located under the epidermis, in particular between the dermis and the bone, and more particularly between the deep dermis and the periostium of the bone.

Before proceeding with the intervention, the practitioner can determine the zones to be treated via a careful examination of the patient, in particular using suitable lighting, in order to detect any lack in volume and the asymmetries that may result from it, but also to detect the blood vessels that should be avoided in order to not create trauma for the patient.

This examination comprises local observations but also a global observation, in particular entailing the face, in order to correct the unsightly effects in a harmonious way and as such guarantee a natural result for the patient. Once the zones to be treated are identified, the practitioner can mark them using a hypoallergenic pencil.

Moreover, in order to limit the risks of infection, the practitioner must obviously take hygienic measures, in particular before proceeding with the marking of the zones to be treated. To do this, the practitioner can clean the skin in order to remove any impurities, in particular maker-up, and apply an antiseptic solution on the skin.

For the injecting of a product, the kit comprises at least one cannula 20 with a blunt tip 20a, the cannula having at least one injection orifice 21 which can in particular be arranged laterally in the vicinity of the blunt tip. In particular, the orifice 21 has a diameter between 0.05 mm and 1 mm and is located at about 2 mm from the blunt tip 20a.

In a known manner, the use of blunt-tip injection cannulas is particularly advantageous within the framework of an aesthetic intervention, in that they make it possible not only to prevent sectioning blood vessels and nerve injury during the inserting thereof under the skin of a patient, and as such limit the trauma for the patient, but also to limit the risk of accidental pricks for the practitioner.

According to the product to be injected, the depth of the area to be treated and/or the location thereof in relation to the access hole, the dimensions of the cannula 20 can vary. In particular, the cannula 20 can have a reduced external calibre if the product is fluid and on the contrary more substantial if the product is thick. For example, the cannula 20 can have an external calibre between 14 G (14 gauges, which corresponds to a diameter of 2 mm) and 33 G (0.2 mm), and in particular between 22 G (0.7 mm) and 25 G (0.5 mm).

The cannula 20 can also have a more or less substantial internal calibre, in particular chosen from among three standard sizes (normal, thin wall, extra-thin wall), the internal calibre having in particular an influence on the pressure applied to the product during the injection. As such, with a thin wall internal calibre, the practitioner can inject a thick product without applying excessive pressure to the product, which makes it possible to facilitate the injecting and to reduce the pain for the patient. Moreover, by applying less pressure, the molecules of the product are less subjected to physical constraints and therefore less likely to be deteriorated.

Moreover, the cannula 20 can have a variable length, according to the depth and/or the location of the area to be treated with the cannula with respect to the access hole. This length can in particular be between 13 mm and 110 mm, and more particularly between 25 mm and 70 mm.

The cannula 20 is advantageously flexible, so as to facilitate the guiding thereof to the area to be treated, then the positioning of its injection orifice 21 in the area to be treated. In particular, the flexibility of the cannula 20 is linked to the external calibre, and in particular to the relation between the external calibre and the internal calibre, the flexibility being all the more so substantial that the relation, and therefore the thickness of the wall of the cannula 20, is reduced.

Furthermore, the cannula 20 can be at least partially made of stainless steel, in particular of SUS 304 alloy or of AISI 304 alloy (of crude chemical formula $FeCr_{18}Ni_{10}$), with the latter being particularly remarkable for its good performance in terms of flexibility, robustness, elasticity, resistance to corrosion and tolerance by the organism of the patient, and/or of a shape-memory alloy.

In addition, the outer surface of the cannula 20 can have been subjected to a special treatment, for example with a silicone base, in order to facilitate the sliding of the cannula under the skin of the patient, and therefore to minimise the trauma for the patient, in particular hematomas, bruises or oedemas.

In a known manner, in order to inject the treatment product, the cannula 20 is mounted on a syringe or another type of container in which a quantity of the product in conditioned.

To do this, the cannula 20 has a base 22 whereon a proximal end 20b of the cannula opposite the blunt tip 20a is mounted, for example by being fixed by means of an adhesive in a housing provided for this purpose on the base, the base intended to be mounted on a tip of a syringe containing the product to be injected.

For example, the base 22 can be of the Luer-Lock® or Luer-Slip® type, to be mounted respectively by screwing or by friction on the tip of the syringe, with these types being advantageously universal in order to allow for the use of the cannula 20 with all types of syringes or other containers. In particular, the base 22 comprises fins 25 in order to make it possible to connect to the container of the syringe type. Alternatively, the base 22 can have a screw pitch.

Moreover, the base 20 can be made from polypropylene or from a polypropylene copolymer, in particular ethylene-polypropylene. Generally, the base 20 can be made from a non-flammable material, in particular devoid of pyrogen.

In order to allow the practitioner to quickly identify the external calibre and/or the internal calibre of the cannula 20, and as such select the cannula according to his needs, the base 22 of the cannula can include an identification marking of its external calibre and/or of its internal calibre.

In particular, the identification marking consists of a coloration of the base 22, with the coloration corresponding to the internal calibre and/or to the external calibre of the cannula 20, such as defined in particular by the standard NF EN ISO 6009.

In order to be able to insert such a cannula 20 under the skin of a patient, the method provides for a step of piercing a zone of the skin, so as to arrange for the cannula 20 an access hole under the skin.

To do this, the kit for injecting comprises a device for inserting the cannula 20 under the skin of the patient, the device comprising a central body 1 equipped with a groove 2 which has a sharp distal tip 2a projecting from a distal end 1a of the body for the piercing of the skin.

Figure 1:
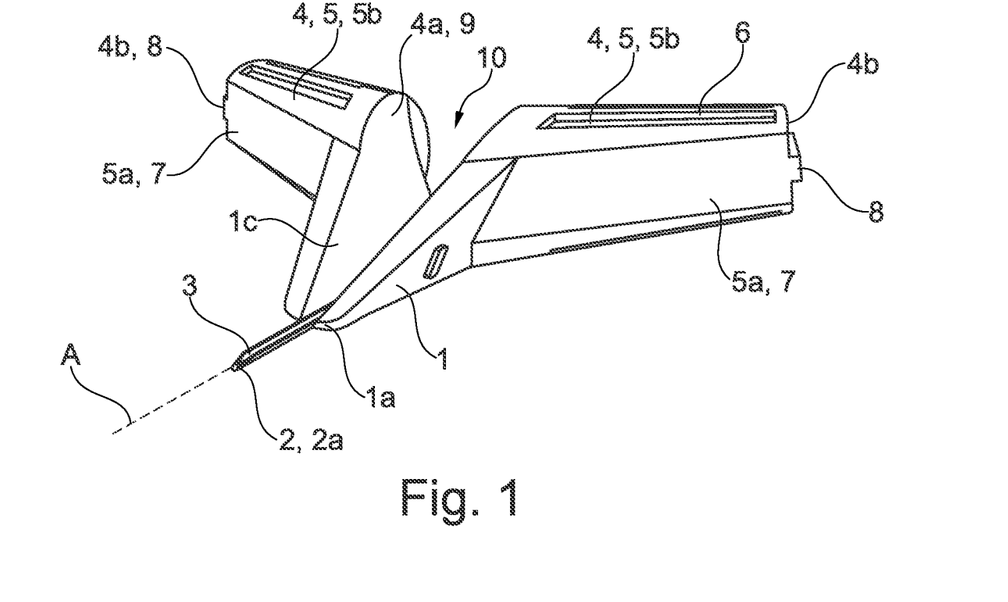
FIG. 1 is a front perspective view of a device for inserting a cannula according to an embodiment of the invention.
Figure 2:
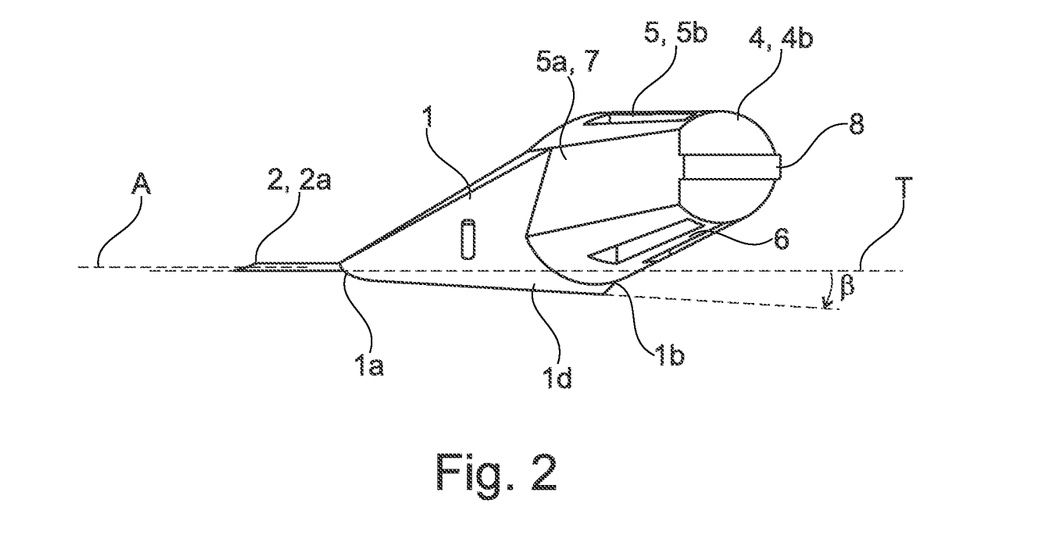
FIG. 2 is a right side view of the device for inserting a cannula of FIG. 1.

In relation with figures, the groove 2 extends along a sagittal plane S that forms a plane of symmetry for the device, and in particular for the central body 1, with the device being shown according to the sagittal plane in FIG. 2.

Figure 3:
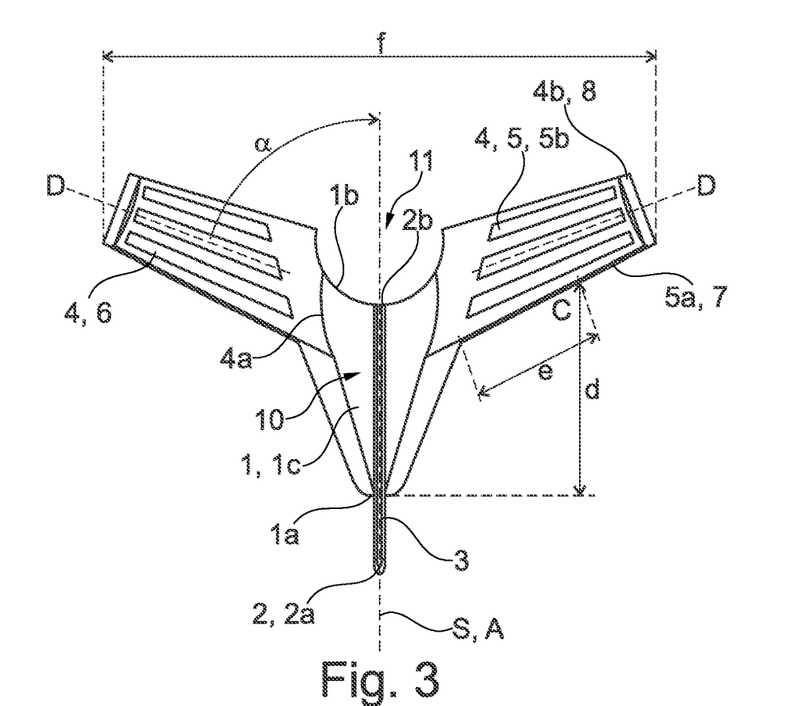
FIG. 3 is a top view of the device for inserting a cannula of FIG. 1.
Figure 4:
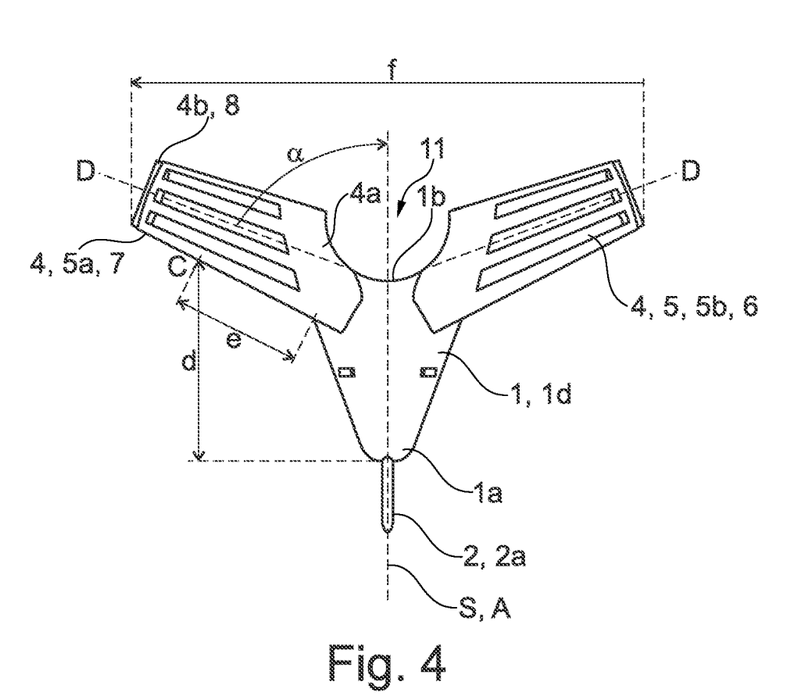
FIG. 4 is a bottom view of the device for inserting a cannula of FIG. 1.
Figure 5:
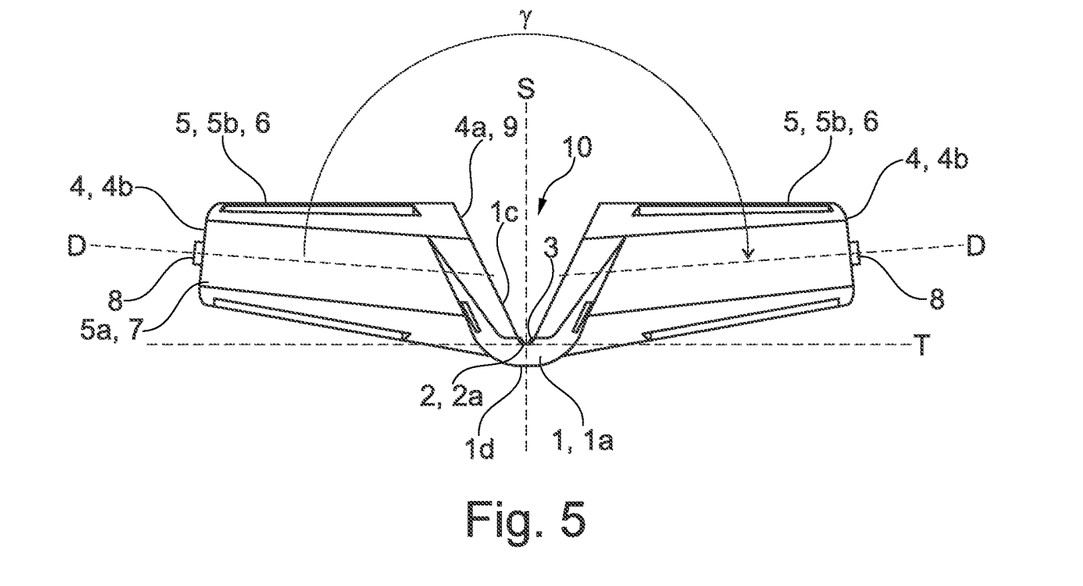
FIG. 5 is a front view of the device for inserting a cannula of FIG. 1.
Figure 6:
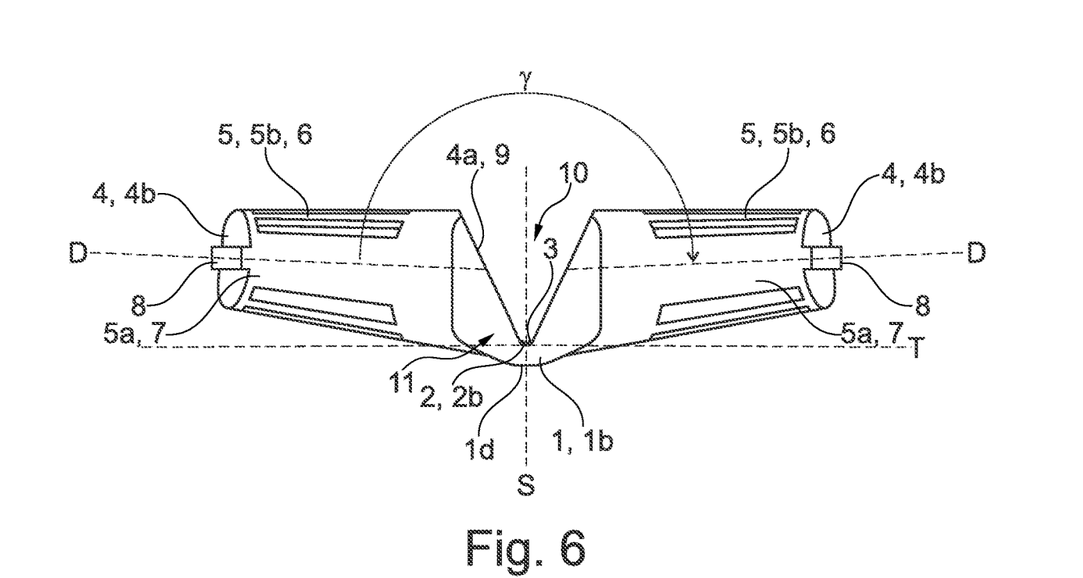
FIG. 6 is a rear view of the device for inserting a cannula of FIG. 1.

The groove 2 furthermore defines:
a transverse plane T which is perpendicular to the sagittal plane S and whereon the groove 2 extends to its distal tip 2a, the transverse plane passing in particular in the distal tip, the device being shown according to the transverse plane in FIGS. 3, 4; and—a frontal plane that extends perpendicularly to the sagittal plane S, the device being shown according to the frontal plane in FIGS. 5, 6.

In particular, the length of the sharp distal tip 2a is limited in order to ensure a penetration of the tip over a limited depth of the skin of the patient, and as such prevent trauma on the tissues and the vessels of the deep layers of the skin, such as hematomas, bruises or oedemas, as well as nerve injury.

The distal end 1a of the central body 1 has a blunt and in particular rounded shape, as well as a flared shape in the transverse plane T, in order to ensure a non-traumatic contact of the distal end against the skin when the sharp tip 2a is entirely inserted into the skin, with such a contact furthermore having the advantage of being psychologically reassuring for the patient.

The zone to be pierced can in particular be located on the face of the patient, for example near an ear (retromandibular point), in a nasolabial zone (on the modiolus, nasolabial point), on the zygomatic bone (zygomatic point), on a temple (temporal or frontal point) or above the glabella (glabellar point). As such, the practitioner can reach several zones to be treated located on the face and/or the neck of the patient from the same hole arranged in the zone to be pierced, which makes it possible to limit the piercings of the skin, and therefore trauma for the patient. In particular, for an intervention on the face, the number of zones to be pierced can be between one and five for each side of the face.

The zone to be pierced can also be located on any other portion of the body of the patient, in particular on a hand, an arm or a thigh, on the chest, in particular on the neckline, on the scalp, on the belly, or on a foot.

To pierce the skin of the patient, the practitioner, after having prepared the skin, grasps the device with his fingers and inserts the sharp distal tip 2a into the skin.

Once the skin of the patient is pierced, the method provides to arrange the injection cannula 20 on the groove 2, with the sharp tip 2a of the device remaining planted in the skin. Then, the method provides a consecutive step of sliding the injection cannula 20 beyond the sharp distal tip 2a, so as to insert the blunt tip 20a under the skin.

To do this, the groove 2 is arranged to allow the sliding along same of the injection cannula 20 beyond its distal tip 2a towards at least one area to be treated located under the skin of the patient. In particular, the groove 2 has an internal dimension that is greater than the external calibre of the injection cannula 20 that is to slide over it.

In relation with figures, the groove 2 has an open proximal end 2b that opens into a proximal wall 1b of the central body 1. As such, particularly intuitively, the method can provide to arrange the cannula 20 on the groove 2 by inserting the blunt tip 20a of the cannula into the proximal end 2b, then to slide the blunt tip over the entire length of the groove 2.

Moreover, the groove 2 has an upper slot 3 which is surrounded by an upper wall 1c of the central body, the slot extending over at least one portion of the length of the groove, and preferably over the entire the length.

In particular, the slot 3 can have a separation that is greater than the external calibre of the cannula 20. As such, in order to be able to slide the cannula 20 over the groove 2, the practitioner can arrange the blunt tip 20a on any point of the groove by inserting the blunt tip laterally via the slot 3, which facilitates the arrangement and allows the practitioner to save time.

Alternatively, the slot 3 can have a separation that is less than the external calibre of the cannula 20, in such a way that the cannula cannot be extracted laterally from the groove 2 via the slot. In this case, in order to arrange the cannula 20 on the groove 2, the practitioner can insert the blunt tip 20a of the cannula only into the proximal end 2b of the groove.

In the embodiment shown, the groove 2 has a geometry of a longitudinal cylinder section, in particular a semicylindrical geometry carried out by means of a half-needle cut longitudinally over all or a portion of its length. As such, the groove 2 has a geometry of shape complementary to that of the injection cannula 20, which makes it possible to facilitate the sliding of the cannula over the groove.

In particular, the inner diameter of the groove 2 depends on the proportion of the diameter to which the cylinder section is carried out, the diameter being all the more so substantial that the proportion is low. As such, when the groove 2 has a semicylindrical geometry, its inner diameter corresponds to the separation of the slot 3 and is greater than the external calibre of the cannula 20, which makes it possible to arrange the cannula on the groove by inserting the blunt tip 20a on any point of the groove.

As such, the practitioner can save time in relation to conventional injection techniques, as he does not have to locate the hole formed by piercing, since the device that was used for the piercing remains positioned in the hole and the access to the area to be treated is materialised by the groove 2, which is easy to locate. Therefore, the practitioner does not need to have recourse to traumatic practices for the patient, such as pinching the skin of the patient several times to locate the hole risking making it bleed.

Furthermore, thanks to the guiding of the cannula 20 by the groove 2, the practitioner searches less during the inserting of the cannula, which is also less traumatic for the patient.

In addition, the operations of manipulating the piercing device are limited, which makes it possible to limit the risks of accidental pricking for the practitioner and the risk of a loss of sterility of the sharp tip 2a of the device.

According to the depth of the area to be treated and/or its location in relation to the access hole, the cannula 20 can be inserted under the skin in varied angular directions with respect to the skin. In particular, the cannula 20 can be inserted in a direction that is substantially tangent to the surface of the skin, in particular if the product has to be injected into a single zone or into several zones that are substantially located on the same path of progression. On the contrary, the cannula 20 can be inserted in a direction that is substantially perpendicular to the surface of the skin, in particular if the product has to be injected into several zones located in clearly different directions. Furthermore, the thickness of the skin and/or its texture can also influence the angle of insertion of the cannula 20.

Consequently, in order to correctly guide the cannula 20 to the zone or zones to be treated, the groove 2, and therefore the device, have to be oriented in the angular direction of insertion of the cannula during the insertion of the sharp tip 2a into the skin, the practitioner having furthermore to maintain the device in the orientation at least until the blunt tip 20a of the cannula is inserted under the skin.

To do this, the central body 1 is provided with two lateral grasping arms 4 of extended shape that extend symmetrically on either side of the sagittal plane S, each grasping arm 4 having a finger grip surface 5.

In particular, the extended shape of the grasping arms 4 and their lateral arrangement on either side of the groove 2 allows the practitioner to easily grasp the device by holding only one of the arms via its finger grip surface 5, in particular on a front central portion 5a and on a rear portion 5b opposite the surface, for example by pinching the arm between his thumb and his index finger.

As such, the hand of the practitioner that holds the device can easily be arranged separate from the axis A of the groove 2 and from the sagittal plane S, and therefore from the guiding axis of the cannula 20, and this without forcing the practitioner to adopt with the main an uncomfortable and potentially painful position in the long term for his wrist. Thanks to this, the practitioner can easily arrange and slide the cannula 20 over the groove 2 using his other hand, without the two hands hindering each other mutually.

In relation with figures, in particular FIGS. 3 and 4, the lateral arms 4 each extend in a transverse direction D which forms with the sagittal plane S an angle α of between 30° and 85°, and in particular of 65°.

This angular range offers a good compromise for both facilitating the maintaining of the device by two-finger grasping of one of its arms 4 and limit the encumbrance of the axis of the groove 2 by the hand maintaining the device.

Indeed, for an optimum maintaining of the device via two-finger grasping, the transverse direction D of the arms 4 must not be excessively separated from the sagittal plane S, in order to not excessively separate the axis of the effort to be provided in order to prick the skin with respect to the axis A of the groove 2. In particular, when the angle α is greater than 85°, the device is unsuitable for a maintaining by two-finger grasping, because such a maintaining generates a cantilevered effect which is inconvenient for the piercing of the skin.

Moreover, the lower the angle α is, the closer the pricking effort of the skin is to the axis A, but in return the hand further occupies the axis A of the groove 2, which is inconvenient for the guiding of the cannula 20. In particular, when the angle α is less than 30°, the ergonomics of the device is compromised in that the hands of the practitioner interfere mutually with one another, which forces the practitioner to adopt with the hand holding the device an uncomfortable and potentially painful posture, for example by arranging the hand substantially flat with respect to the skin of the patient and according to a hardly natural angle in relation to his wrist.

Advantageously, the angle α is between 45° and 80°, and more particularly between 65° and 80°, which confers optimum ergonomics to the device.

Furthermore, for an angle α between 30° and 40°, the shape of the arms 4 can be adapted to further release the axis A for guiding the cannula. In particular, the arms 4 can have a curved shape in their transverse direction D, with the radius of curvature of the shape being furthermore sufficiently substantial, in particular greater than 20 mm, in order to facilitate the grasping of the arms 4.

Moreover, each grasping arm 4 has a proximal end 4a integral in the vicinity of the proximal wall 1b of the central body 1, with the front central portion 5a of each arm 4 having a centre C that extends at a distance e of about 10 mm from the proximal end, the centre corresponding to the epicentre of the pressure exerted by the finger when the practitioner grasps the arm 4. Note that the length of each arms 4 does not substantially influence the ergonomics and therefore does not substantially influence the position of the epicentre C.

In particular, the front central portion 5a of each finger grip surface 5 is located, in particular on its epicentre C, at a distance d between 8 mm and 30 mm from the distal end 1a of the central body 1, with such a range of values corresponding to the average thicknesses of a finger.

As such, when the practitioner holds the device by placing his index finger on the front central portion 5a of the finger grip surface 5 of an arm 4 and his thumb on the rear portion 5b of the surface, then pricks the skin by maintaining the device as such, his index finger is placed between the skin and the arm, in particular when the sharp tip 20a is inserted according to an angle that is substantially perpendicular to the skin, and this without hindering the insertion. Moreover, if the distance d is sufficiently small, the index finger can be as close as possible to the skin, and in particular bearing against the grasping arm 4 and the skin, which provides better stability to the device and facilitates the maintaining thereof during the inserting of the cannula 20 under the skin.

In particular, the distance d is between 10 and 25 mm, and in particular equal to 13 mm, which provides the device with optimum ergonomics. When the distance d is located below 8 mm, the device is unsuitable for a two-finger grasping of an arm 4, in that the finger bearing on the front central portion 5a would interfere with the piercing of the skin. Moreover, a distance d located beyond 30 mm does not allow the practitioner to rest his finger against the skin during the piercing, and therefore has a negative impact on the precision of the piercing.

In relation with FIGS. 1 to 6, in order to facilitate the grasping thereof, the arms 4 each have a volume geometry, and in particular a substantially cylindrical geometry around their transverse direction D. As such, the practitioner can grasp the device in a varied manner, according to his preferences, his body position in relation to the patient, the zone to be pierced and/or the angular direction according to which the cannula 20 must be inserted.

Alternatively, as shown in the FIGS. 8 to 11, the arms 4 can have a geometry with flatter shapes, in particular a rectangular geometry, in order to facilitate the two-finger grasping of the arms.

In particular, the arms 4 have a slightly truncated-cone geometry, which allows for a relaxed and precise posture of the index finger and of the thumb of the practitioner in order to grasp the arms with two-finger grasping, and this whether the practitioner is left handed or right handed. Moreover, the practitioner can, via small rotations, position via successive searching the sharp distal tip 2a and adjust its angular direction of insertion under the skin.

In order to facilitate these small rotations, in particular by preventing the fingers of the practitioner from sliding on the finger grip surfaces 5, the surfaces each have at least one portion whereon extend a succession of patterns in relief 6 for assistance with finger gripping. In the FIGS. 1 to 6, the patterns 6 extend in the transverse direction D of an arm 4. Alternatively, the patterns 6 can have another configuration, in particular by extending in another direction, for example perpendicular to the transverse direction D.

In relation with FIGS. 1 to 6, each finger grip surface 5 has a front flat surface 7, whereon is formed the front central portion 5a, as well as a succession of patterns in relief 6 that extend over the rear portion 5b opposite the front flat surface. As such, the practitioner can grasp an arm 4 by placing his index finger on the front flat surface 7, which provides good stability to the index finger, and his thumb on the rear portion 5b, in order to carry out small rotations using only the thumb, and as such accurately position the sharp tip 2a.

Moreover, each grasping arm 4 has a distal end 4b whereon is formed a pattern in relief 8 for assisting with the finger grip. As such, the practitioner can also hold the device by pinching the distal ends 4b of each arm 4 with respectively his thumb and his index finger, with the patterns in relief 8 allowing for the maintaining without pivoting of the device between the fingers.

In particular, the patterns 8 can have the form of a rectangle passing through the centre of respectively a distal end 4b, as shown in the figures, but also in other forms, such as for example an off-centred lug or two cut sections.

Furthermore, the distal ends 4b of each arm 4 are separated from one another by a distance f of about 34 mm in the transverse plane T, in order to allow the practitioner to pinch the ends with a correct separation between his fingers, i.e. a separation that is neither excessively large, in order to not generate fatigue in the long term, or excessively small, in order to not hinder the guiding and the inserting of the cannula 20 under the skin.

In relation with FIG. 2, the central body 1 has a lower portion 1d that extends under the transverse plane T by forming with the transverse plane, and therefore with the sharp tip 2a, an angle β. As such, by limiting the extend of the material of the body 1 under the axis A of the groove 2, and therefore under the sharp tip 2a, the device can be oriented in such a way as to insert the sharp tip 2a in a direction tangent to the surface of the skin, so as to be able to insert a cannula 20 in such a direction.

The angle β can have a very low value, even practically zero, as shown in FIGS. 8 to 11. However, it occurs that the practitioner wants to slide the device along the skin prior to piercing, so as for example to reflect on the exact location of the piercing, and an angle β that is excessively low would make this manipulation more delicate, in that the practitioner could inadvertently pierce the skin at an inappropriate location.

The angle β can also have a more substantial value, but must not exceed 15°, otherwise the device will be unsuitable for a tangent piercing of the skin.

In particular, for an angle β between 0 and 6°, and in particular equal to 3°, the device has optimum ergonomics. Moreover, concerning the possibility of tangential piercing, it is generally correct for an angle β less than or equal to 12°.

In order to improve access to the groove 2, and therefore facilitate the arrangement of the cannula 20 on the groove, the upper wall 1c of the body 1 has a clearance zone 10 that extends on either side of the groove.

In relation with figures, the central body 1 has a geometry in the shape of a V, with the upper wall 1c as such forming a flared channel at the centre of which the groove 2 is arranged. Moreover the proximal ends 4a of the grasping arms 4 each have a slope 9 that extends in the extension of respectively a section of the upper wall 1c, in such a way that the proximal ends form with the upper wall the upper clearance zone 10 of access to the groove 2.

Furthermore, the grasping arms 4 extend in relation to one another in the frontal plane according to an angle γ between 90° and 180°, and in particular of 172°, with such an angular range making it possible to satisfactorily ensure access to the groove 2 via the upper clearance zone 10.

Likewise, the proximal wall 1b of the central body 1 is surrounded by a rear clearance zone 11 arranged to allow for the use of an injection cannula 20 of short length, in particular by avoiding the risks of collision between the proximal wall 1b of the body 1 and of the base 22 of the cannula when the latter is slid on the groove 2, then inserted under the skin of the patient.

In relation with figures, the rear clearance zone 11 has a shape of an arc of a circle and extends on either side of the proximal wall 1b of the body 1, in particular by extending over the proximal ends 4a of the grasping arms 4. In particular, the rear clearance zone 11 has a radius of curvature of about 5 mm.

Once the cannula 20 inserted under the skin, the method can provide for removing the device in order to extract its sharp tip 2a from the skin, and this while leaving the cannula 20 inserted under the skin. In particular, the method can provide to remove the device by sliding the groove 2 with respect to the cannula 20 inserted under the skin.

After having removed the device, the practitioner has the use of both hands to finish positioning the cannula 20, in particular by sliding the cannula under the skin until its injection orifice 21 reaches an area to be treated, in order to be able to inject the product into the zone.

In order to facilitate the positioning of the injection orifice 21 in the area to be treated, in particular when the latter is located at a substantial depth and/or at a substantial distance from the access hole, the cannula 20 can have graduations 23 arranged at regular intervals over its length, for example every centimetre.

Moreover, the base 22 of the cannula 20 can comprise on its periphery a marking 24 for locating the injection orifice 21 which is aligned with the injection orifice, which allows the practitioner to correctly orient the injection orifice when the latter is positioned in the area to be treated.

Figure 7:
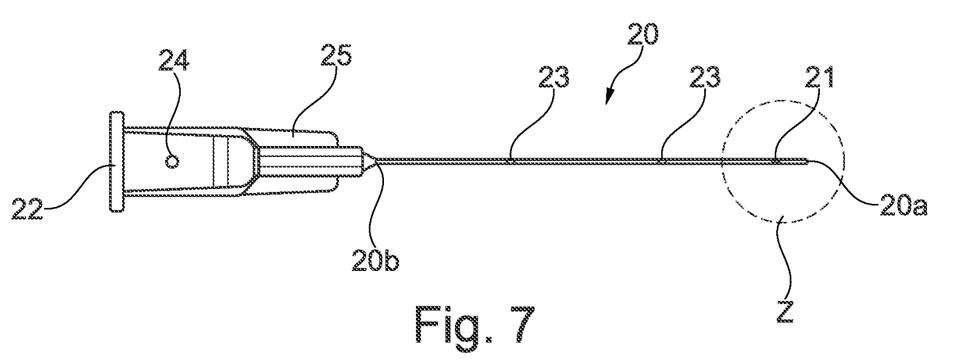
FIG. 7 shows an injection cannula that can be used in a kit for injecting with the device of FIGS. 1 to 6.
Figure 7A:
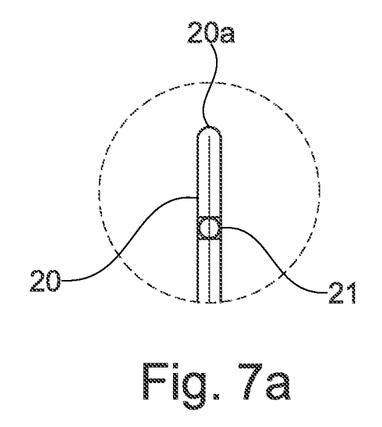
FIG. 7*a* is an enlarged view of the zone Z of FIG. 7.
Figure 8:
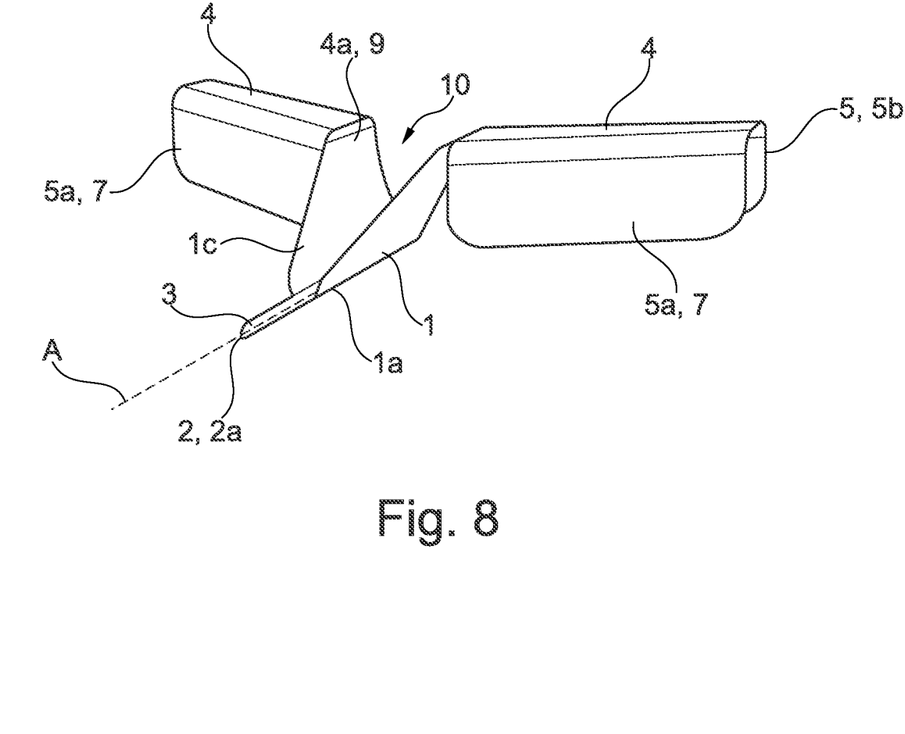
FIG. 8 is a front perspective view of a device for inserting a cannula according to an alternate embodiment of the invention.
Figure 9:
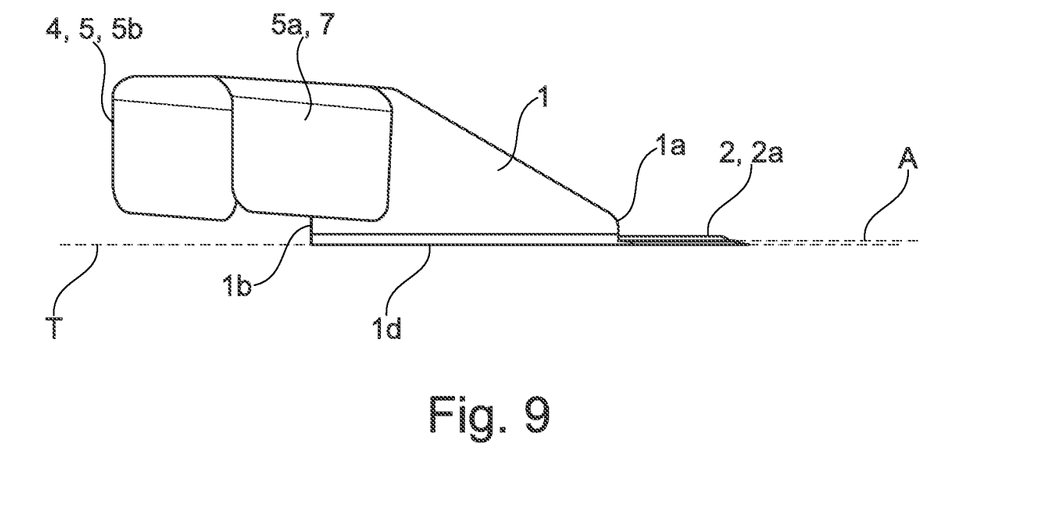
FIG. 9 is a side view of the device for inserting a cannula of FIG. 8.
Figure 10:
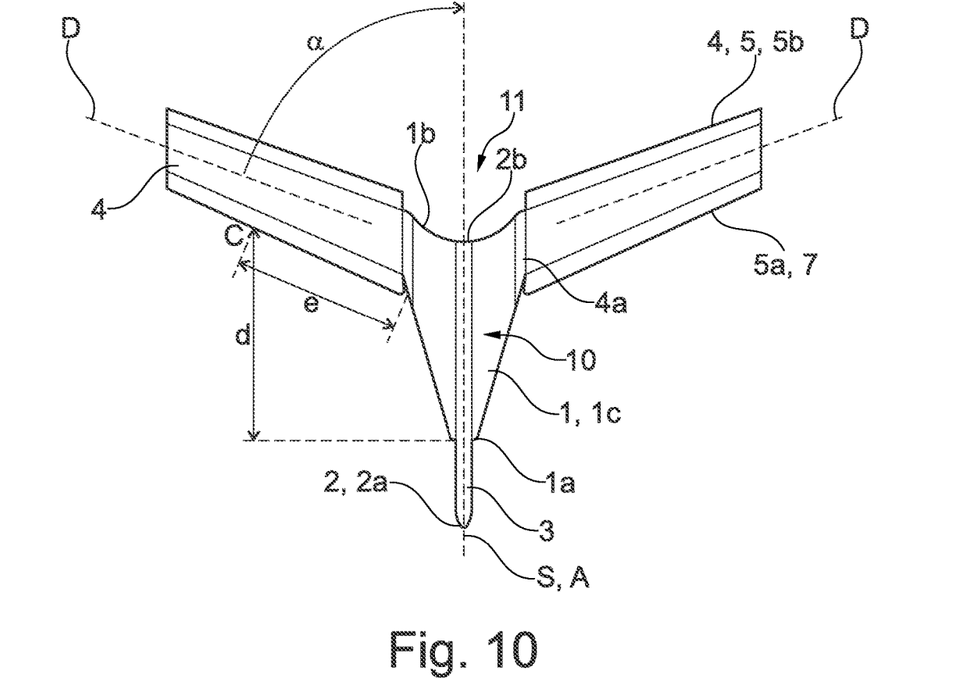
FIG. 10 is a top view of the device for inserting a cannula of FIG. 8.
Figure 11:
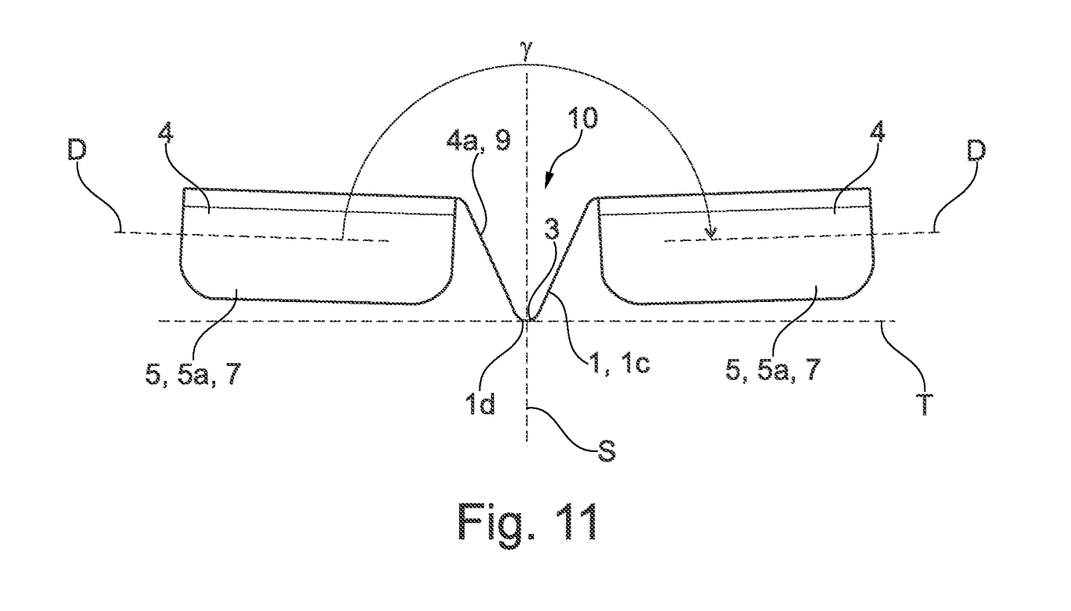
FIG. 11 is a front view of the device for inserting a cannula of FIG. 8.

In relation with FIG. 7, the marking for locating comprises a point 24 arranged on the periphery of the base 22, the point being carried out in a colour that is sufficiently easy to see to contrast with the colour of the base.

Alternatively, the marking for locating 24 can have another pattern, in particular in the form of an arrow. It can furthermore be carried out in relief on the base 22, for example during the moulding of the base, and possibly coloured with a tint that is different from the base.

In order to limit the pain felt by the patient during the intervention, the method can provide a step prior to the piercing of the skin, in which an anaesthetic product is applied at least on and/or in the zone to be pierced, which makes it possible to limit both the pain due to the piercing and the pain due to the inserting of the cannula 20. In particular, the anaesthetic product can be applied locally in the form of a cream and/or patch, for example a patch of the Emla® type.

Moreover, the method can provide to treat several zones successively, and this by accessing therein using the same access hole. In particular, for the injecting of the same product into several zones to be treated, the method can provide to displace a cannula 20 already inserted in the skin of the patient to another area to be treated after injection of the product into a first zone.

In particular, the method can provide for a radial displacement between the zone that has just been treated and a new area to be treated in order to proceed with a new injection into the new zone.

Furthermore, the method can provide to repeat at least once such a radial displacement from the treated zone to another area to be treated and a consecutive step of injecting product into the other zone. As such, the practitioner can treat an entire zone of the face, for example the forehead, a temple or a cheek, and this using a single access hole.

In order to correct a slackening of the skin widely extended over a zone of the face, for example on the forehead, on a temple or on a cheek, a known technique consists in injecting the product by bolus injection, i.e. placing several small doses of product on over the entire the zone by carrying out several displacements in the zone, in order to stretch the skin over the entire zone while still giving it volume.

In particular, the practitioner can proceed with several injections via bolus injection by carrying out several radial displacements, in particular as a fan, in the same zone, then massage. The practitioner can also use a particular technique called "topping" which is generally carried out in a layer of the hypodermis, in order to perform a smoothing on the surface and to plump the skin in depth.

By radially displacing the cannula 20 already inserted in the hypodermic layer from an already treated zone of the layer to another area to be treated, the cannula remains in particular at a constant depth. As such, the practitioner is assured of carrying out all of the topping injections in the same layer, and in particular at a same depth in the layer.

Thanks to this, the practitioner can easily plump a layer under the skin with a constant thickness of product, which makes it possible to guarantee the homogeneity and the harmony of the final result.

Moreover, the method can provide to displace the cannula 20 to the rear during the injection by bolus injection of the product, i.e. according to a retrograde movement, in order to distribute the product over a substantial interval of depths and/or over a wider zone, which allows for a more harmonious and therefore more natural result. Alternatively, the method can provide to displace the cannula 20 to the front, according to an antegrade movement, during the injection by bolus injection of the product.

Once the injections are completed, the practitioner removes the cannula 20 and can perform a massage on the treated zone, in order to evenly distribute the product and give a more homogeneous and therefore more natural aspect to the correction made. The patient can then observe results that are immediately visible and sustainable.

In relation with FIGS. 8 to 11, the groove 2 is formed of a single piece with the body 1 using a sheet of suitable material, in particular made of metal, and more particularly made of stainless steel such as the SUS 304 alloy and/or the AISI 304 alloy. To do this, a suitable shape can be cut in such a sheet, then formed in three dimensions by stamping the cut sheet.

In particular, the stamping makes it possible to generate by creeping variable thicknesses of material, in particular a low thickness of material on the groove 2 and a more substantial thickness of material on the central body 1 and the arms 4.

Furthermore, the stamping can be supplemented with stretching of material, in order to obtain a device with richer shapes in three dimensions. As such, one can for example connect the reliefs of the arms 4 to the reliefs of the central body 1 and obtain better rigidity of the device as a whole while still remaining in thin thicknesses.

In particular, the groove 2 can benefit from a sharpening after the stamping in order to form and/or sharpen the sharp distal tip 2a.

In relation with FIGS. 1 to 6, the groove 2 and the body 1 can be formed from a single piece by injection of a suitable material, in particular a plastic material. In particular, the plastic material can comprise a polymer that is inoffensive for the human or animal body, in particular by being implantable, for example polypropylene or a copolymer with a polypropylene base, such as ethylene-polypropylene. Generally, the groove 2 and the body 1 can be made from a non-flammable material, in particular devoid of pyrogen.

The groove 2 can also be formed in a separate piece added onto the body 1, for example by gluing of the groove onto the body or by overmolding of the groove by the body.

In order to facilitate the reliable positioning of the groove 2 in the body 1 during the gluing, an extra thickness can be provided, preferentially from 3 to 5 mm long, in the proximal portion of the upper wall 1c forming a flared channel. This extra thickness can be pierced with a hole that can receive the groove 2, so that the latter is retained and positioned in a forced and reliable manner during the gluing. The extra thickness must be of low thickness, preferentially less than 15/10 of a millimetre so that it does not interfere when the practitioner inserts the cannula into the hole made by the device.

In order to facilitate the fastening of the groove 2 to the body 1, the proximal end 2b of the groove can be initially integral with a tubular element by means of a frangible link, the element being formed of a single piece with the groove.

In particular, the tubular element forms a means for grasping, for example for a robotic arm within the framework of industrial series production, in order to maintain the groove 2 during its fastening to the body 1. As such, the presence of such a grasping element makes it possible to avoid the grasping of the groove 2 via its sharp tip 2a, and as such damaging the sharp edge of the tip. Such an element also makes it possible to avoid the grasping of the groove 2 by its proximal end 2b, with such a grasping making it difficult and even impossible to fasten the groove onto the body 1.

Once the groove 2 is integral with the body 1, the tubular element is separated from the groove by breaking the frangible link, for example by pivoting the tubular element with respect to the groove around the frangible link.

However, after the breakage of the frangible link, debris of material can remain on the proximal end 2b of the groove 2, the debris furthermore able to be relatively sharp and have a risk of injury for the practitioner. In order to limit the contact of such debris with the fingers of the practitioner, the proximal wall 1b of the central body 1 can have a recess above which opens the proximal end 2b of the groove 2, the recess having a dimension according to the axis A of the groove which is arranged in order to prevent such debris from projecting beyond the recess.

The grasping arms 4 can also be formed in a single piece with the central body 1 and/or the groove 2, in particular by methods such as described hereinabove.

The grasping arms 4 can also be added onto the central body 1, in particular by overmolding. In particular, the central body 1 can be formed by stamping with two lateral armatures that extend symmetrically on either side of the sagittal plane S, as shown in FIGS. 8 to 11, then the armatures can be coated with a volume of material, for example by overinjection of the material on the armatures, in order to form the grasping arms 4.

The device manufactured as such can then be conditioned with at least one blunt-tip 20a cannula 20 in order to form a kit for injecting. To do this, the device and the cannula 20 of the same kit can be conditioned in the same sterile transparent bag, in particular with a polypropylene and/or polyethylene base, the bag furthermore being able to be flexible or rigid and/or include at least one portion with a peeling paper base.

Moreover, the kit conditioned as such can be stored in a box containing other kits also conditioned in bags, in order to be protected from humidity and from light during the storage thereof.

In particular, the central body 1 of the device can have a coloration identical to that of the base 22 of the cannula 20, which makes it possible to identify the device and the cannula as belonging to the same kit for injecting. Therefore, the practitioner can identify, among several kits conditioned in bags, the kit that he needs simply by looking at the colour of the base 22 and of the central body 1.

The device can also be conditioned alone, in particular in a bag such as described hereinabove, in order to be marketed alone, in particular for sale to laboratories.

Moreover, after the conditioning in a bag, the device or the device/cannula 20 kit are sterilised, for example using a method of sterilisation via ethylene oxide (ETO), via ionising radiation or via steam.

In addition, the bag can include indications for the practitioner, such as a lot number, the dimensions of the cannula 20 and/or of the device, a notion restricting use to qualified practitioners, a reference to the notified organisation and/or a conformity marking with a standard, in particular the CE standard.

In particular, the bag can include information useful for a use without danger of the device or of the device/cannula 20 kit that it contains, for example a sterilisation date and/or an expiry date. Moreover, if the bag has a poor conditions and/or an opening, the practitioner can immediately know that the device or the kit contained in the sachet must be destroyed for the safety of the patient.

The invention claimed is:

1. A device for inserting a blunt-tip cannula under a skin of a patient with a view to injecting a biocompatible product, said device comprising a central body equipped with a groove that extends along a sagittal plane (S) while having a sharp distal tip projecting from a distal end of said central body in order to pierce said skin, said groove being arranged to allow the blunt-tip cannula to slide along beyond said distal tip towards at least one area to be treated located under said skin, the central body being provided with two lateral grasping arms that extend symmetrically on either side of the sagittal plane in a transverse direction that forms, with said sagittal plane, an angle (a) of between 30° and 85°, each of the two lateral grasping arms further having a proximal end with a slope and a finger grip surface that has a front central portion located at a distance between 8 mm and 30 mm from the distal end of the central body, the central body further including a V-shaped geometry and an upper wall forming a flared channel at a center of which the groove is arranged, the upper wall having a clearance zone configured to facilitate arrangement of the blunt-tip cannula on the groove, the clearance zone formed by the flared channel of the upper wall and the slopes of the proximal end of each lateral grasping arm, the slopes of the proximal ends extending in a section of the upper wall, and the proximal end of each lateral grasping arm integral with and extending from a proximal wall of the V-shaped central body, and wherein the groove includes an upper slot which is surrounded by the upper wall of the central body and that extends along an entire length of the groove, which extends from the sharp distal tip projecting from the distal end of the central body to the proximal wall of the central body.

2. The device according to claim 1, the groove defining a transverse plane which is perpendicular to the sagittal plane, said groove extending to the sharp distal tip, said transverse plane passing through said sharp distal tip, with the central body having a lower portion that extends under said transverse plane by forming with said transverse plane an angle (β) less than or equal to 15°.

3. The device according to claim 1, the groove having an open proximal end that opens into the proximal wall of the central body, said proximal wall being surrounded by a rear clearance zone.

4. The device according to claim 1, the distal end of the central body having a blunt shape.

5. The device according to claim 1, each of the two lateral grasping arms having a substantially cylindrical geometry around its transverse direction.

6. The device according to claim 1, each finger grip surface having a front flat surface whereon is formed the front central portion.

7. The device according to claim 1, the upper wall having the clearance zone that extends on either side of the groove.

8. A kit for injecting a biocompatible product, said kit comprising a device for inserting according to claim 1 as well as at least one blunt-tip injection cannula, the groove being arranged to allow for the sliding of said at least one blunt-tip injection cannula beyond the sharp distal tip towards at least one area to be treated located under the skin of the patient.

9. The kit for injecting according to claim 8, the at least one blunt-tip injection cannula having at least one injection orifice, said at least one injection orifice being arranged laterally in a vicinity of a blunt tip.

10. The kit for injecting according to claim 8, the groove having an internal dimension that is greater than an external calibre of the at least one blunt-tip injection cannula that has to slide over it.

11. A method for injecting within a framework of an aesthetic intervention of a biocompatible product by means of a kit according to claim 8, said method providing for the following successive steps of:
    grasping the device by an intermediary of the finger grip surface of at least one of the two lateral grasping arms;
    piercing a zone of the skin of the patient by means of the sharp distal tip;
    arranging the at least one blunt-tip injection cannula on the groove;
    sliding said at least one blunt-tip injection cannula beyond the sharp distal tip, so as to insert a blunt tip under the skin; and
    removing the device in order to extract the sharp distal tip from the skin by leaving the at least one blunt-tip cannula inserted under said skin.

12. The method for injecting according to claim 11, further including arranging the at least one blunt-tip injection cannula on the groove by inserting the blunt tip of said at least one blunt-tip injection cannula into a proximal end of said groove.

13. The method for injecting according to claim 11, further comprising arranging the at least one blunt-tip injection cannula on the groove by inserting the blunt tip laterally through a slot that extends over at least one portion of a length of said groove.

* * * * *